(12) United States Patent
Murphy et al.

US010549062B2

(10) Patent No.: US 10,549,062 B2
(45) Date of Patent: Feb. 4, 2020

(54) DEVICE FOR THE TREATMENT OF, TREATMENT OF COMPLICATIONS ARISING FROM, AND/OR PREVENTION OF RESPIRATORY DISORDERS CAUSED BY BACTERIAL, VIRAL, PROTOZOAL, FUNGAL AND/OR MICROBIAL INFECTIONS, PREFERABLY FOR THE TREATMENT OF COMPLICATIONS ARISING FROM CYSTIC FIBROSIS

(71) Applicant: LINDE AG, Munich (DE)

(72) Inventors: Paul Murphy, Munich (DE); Syed Jafri, London (GB); Wolfgang Schmehl, Grunwald (DE)

(73) Assignee: LINDE AKTIENGESELLSCHAFT, A GERMAN CORP, Munich (DE)

( * ) Notice: Subject to any disclaimer, the term of this patent is extended or adjusted under 35 U.S.C. 154(b) by 130 days.

(21) Appl. No.: 15/305,790

(22) PCT Filed: Apr. 23, 2015

(86) PCT No.: PCT/EP2015/058861
§ 371 (c)(1),
(2) Date: Oct. 21, 2016

(87) PCT Pub. No.: WO2015/162232
PCT Pub. Date: Oct. 29, 2015

(65) Prior Publication Data
US 2017/0043115 A1    Feb. 16, 2017

(30) Foreign Application Priority Data
Apr. 23, 2014  (EP) .................................... 14165681

(51) Int. Cl.
*A61M 16/12* (2006.01)
*A61K 33/00* (2006.01)
(Continued)

(52) U.S. Cl.
CPC .......... *A61M 16/12* (2013.01); *A61K 9/0073* (2013.01); *A61K 33/00* (2013.01); *A61M 16/009* (2013.01);
(Continued)

(58) Field of Classification Search
None
See application file for complete search history.

(56) References Cited

U.S. PATENT DOCUMENTS 5,839,433 A * 11/1998 Higenbottam ........ A61M 16/00
128/204.21
2006/0191535 A1* 8/2006 Shaffer ................. A61M 16/00
128/204.18

FOREIGN PATENT DOCUMENTS

WO    WO-2006-110923 A2    10/2006

OTHER PUBLICATIONS

"Cystic Fibrosis Symptoms and Treatment", Children's Hospital of Pittsburgh accessed online on Feb. 19, 2019 at http://www.chp.edu/our-services/transplant/liver/education/liver-disease-states/cystic-fibrosis. (Year: 2019).*
Schairer et a. "The potential of nitric oxide releasing therapies as antimicrobial agents", Virulence, May 1, 2012 3(3): 271-279. (Year: 2012).*
International Search Report dated Jun. 29, 2015 for International application No. PCT/EP2015/058861.
Dembinski et al. "Effectiveness of nitric oxide during spontaneous breathing in experimental lung injury", Informa Healthcare, 2010, 8 pgs.

(Continued)

*Primary Examiner* — Carlos A Azpuru
*Assistant Examiner* — Casey S Hagopian
(74) *Attorney, Agent, or Firm* — Adsero IP (57) ABSTRACT

The present invention pertains to a device (1) for the treatment of, treatment of complications arising from, and/or preventing respiratory disorders caused by bacterial, viral, protozoal, fungal and/or microbial infections, preferably for the treatment of complications arising from cystic fibrosis (CF), including a positive airway pressure device (2) for providing a breathing gas under a positive pressure to a patient interface (20), a source of nitric oxide (3) for providing gaseous nitric oxide, a gas injector (4) for inject- (Continued)

ing nitric oxide provided by the source of nitric oxide (3) into the breathing gas provided by the positive airway pressure device (2) under pressure, a flow rate sensor (5) for sensing the flow rate of the breathing gas provided to the patient interface (20) under positive airway pressure, and a controller (6) programmed for controlling the gas injector (4) for injecting the nitric oxide into the breathing gas provided by the positive airway pressure device (2) when a flow rate detected by the flow rate sensor (5) exceeds a predetermined threshold flow rate.

15 Claims, 2 Drawing Sheets (51) Int. Cl.
    *A61K 9/00*     (2006.01)
    *A61M 16/00*     (2006.01)
    *A61M 16/06*     (2006.01)
    *A61M 16/20*     (2006.01)

(52) U.S. Cl.
    CPC .......... *A61M 16/06* (2013.01); *A61M 16/209* (2014.02); *A61M 2016/0039* (2013.01); *A61M 2202/0275* (2013.01)

(56) References Cited

OTHER PUBLICATIONS

Lindwall et al. "Delivery characteristics of a combined nitric oxide nasal continuous positive airway pressure system", Pediatric Anesthesia, 2002, 7 pgs.

Lindwall et al. "A pilot study of inhaled nitric oxide in preterm infants treated with nasal continuous positive airway pressure for respiratory distress syndrome", Intensive Care Med, 2005, 6 pgs.

Putensen et al. "Continuous Positive Airway Pressure Modulates Effect of Inhaled Nitric Oxide on the Ventilation-Perfusion Distributions in Canine Lung Injury", Chest, 1994, 7 pgs.

Trevisanuto et al. "Feasibility of nitric oxide administration by neonatal hulmet-CPAP; a bench study", Pediatric Anesthesia, 2007, 5 pgs.

Welzing et al. "CPAP combined with inhaled nitric oxide for treatment of lung hypoplasia and persistent foetal circulation due to prolonged PPROM", Elsevier, Early Human Development, 2011, 4 pgs.

Communication pursuant to Article 94(3) EPC, (EP Application No. 15 720 035.3) dated Nov. 9, 2018, 6 pages.

\* cited by examiner

DEVICE FOR THE TREATMENT OF, TREATMENT OF COMPLICATIONS ARISING FROM, AND/OR PREVENTION OF RESPIRATORY DISORDERS CAUSED BY BACTERIAL, VIRAL, PROTOZOAL, FUNGAL AND/OR MICROBIAL INFECTIONS, PREFERABLY FOR THE TREATMENT OF COMPLICATIONS ARISING FROM CYSTIC FIBROSIS

RELATED APPLICATIONS

This application is a 35 U.S.C. § 371 national phase application of PCT/EP2015/058861 (WO 2015/162232), filed on Apr. 23, 2015, entitled "Device for the treatment of, treatment of complications arising from, and/or prevention of respiratory disorders caused by bacterial, viral, protozoal, fungal and/or microbial infections, preferably for the treatment of complications arising from cystic fibrosis", which application claims the benefit of European Application No. EP 14 165 681.9, filed Apr. 23, 2014, which is incorporated herein by reference in its entirety.

TECHNICAL FIELD

The present invention pertains to the use of nitric oxide for the production of an inhalable medicament for the treatment of, treatment of complications arising from, and/or prevention of respiratory disorders caused by bacterial, viral, protozoal, fungal and/or microbial infections in a mammal under positive airway pressure as well as to a device for the treatment of, treatment of complications arising from, and/or prevention of respiratory disorders caused by bacterial, viral, protozoal, fungal and/or microbial infections, preferably for the treatment of complications arising from cystic fibrosis.

TECHNOLOGICAL BACKGROUND

In pure form, nitric oxide (NO) is a highly reactive gas having limited solubility in aqueous media (see U.S. Pat. No. 6,164,276). Therefore NO is difficult to introduce into biological systems without premature decomposition. Consequently, administration is typically in the form of a pro-drug which is metabolically degraded to release NO. However, diseases affecting the respiratory tract may be treated by direct inhalation of gaseous NO (IgNO), diluted with an inert carrier gas. In such cases, not only must the potential hazards noted below be avoided, but in many respiratory diseases the bronchioles and alveoli may be constricted by smooth muscle contraction or obstructed by inflammation, thereby reducing access of the therapeutic gas to the desired location(s).

In vivo, NO exhibits multiple effects in a variety of tissues, its range of biological functions including smooth muscle relaxation, neurotransmission, down-regulation of NFκB production to regulate the immune response and to inhibit leukocyte adhesion, regulation of cellular oxygen consumption through effects on mitochondrial respiration, inhibition of platelet aggregation, as well as influencing host defence and cellular differentiation (see Lindwall, R B I, "*Respiratory Distress Sydrome: Aspects of Inhaled Nitric Oxide, Surfactant and Nasal CPAP*"; PhD thesis, (2005; pub. Karolinska Inst., Div. Anaesthesia and Intensive Care; Stockholm, Sweden)).

NO is synthesized by both constitutive and inducible isozymes of the nitric oxide synthases (NOS), which catabolize L-arginine to NO and citrulline. Endothelial constitutive NOS (eNOS), present in the walls of bronchioles and pulmonary arterioles provide NO at nanomolar concentrations for regulating vessel tone. Isozymes of inducible NOS (iNOS) are present in many cell types; upon activation they temporarily produce NO at micromolar concentrations, an activity which, under pathological conditions, has been associated with production of superoxides, peroxynitrites, inflammation and cellular damage.

Endogenously induced NO oxidizes the iron atom of a haem moiety in the enzyme soluble guanylate cyclase (SGC) in the smooth muscle cells of the lower respiratory tract airways, in the pulmonary arteries and in the membranes of circulatory platelets, thereby activating the SGC. The activated SGC forms the second messenger cGMP, which in smooth muscle cells promotes calcium-dependent relaxation, causing vasodilation of blood vessels in the lower respiratory tract, thereby increasing blood flow through the pulmonary arteries and capillaries, and also dilation of the airways in the lower respiratory tract, thereby improving bulk gas transport into the alveoli and exchange of $O_2$ and $CO_2$. A further result is reduction of platelet aggregation on irregular surfaces (such as a constricted blood vessel) thereby lowering the probability of thrombosis (see WO 95/10315 A1).

Other functions of NO are as a neurotransmitter in the brain where it mediates the actions of the excitatory neurotransmitter glutamate in stimulating cGMP concentrations, and in the intestine where it promotes neuronal relaxation. NO also forms nitrosyl derivatives of tyrosine residues in certain functional proteins. However, tyrosine nitration, resulting from reaction of protein tyrosine residues with $NO_2$ or the peroxynitrite anion, is used as an indicator of cell damage, inflammation and NO production. In many disease states, oxidative stress increases the production of superoxide ($\bullet O_2^-$).

The toxicity of IgNO is associated with a variety of properties.

(a) Firstly, NO is swiftly absorbed by lung tissue and enters the blood stream, where it reacts very rapidly with haemoglobin, oxidizing the iron atom of one of the four haem moieties to the ferric form, thereby creating stable methaemoglobin (+ nitrite and nitrate ions). Methaemoglobin's three ferrous haem groups have far greater affinity for oxygen than the haemoglobin haem moieties, so that blood in which the proportion of methaemoglobin is elevated releases insufficient oxygen to the tissues.

(b) Secondly, in the presence of oxygen NO reacts rapidly to form nitrous oxide ($NO_2$), itself a toxic molecule. Gaseous $NO_2$ at 5 ppm is considered to be a dangerously toxic concentration, compared to standard administrations of IgNO at 10 to 120 ppm. As lung disease frequently causes reduced respiratory function, patients are often administered an $O_2$-enriched air supply. In the presence of such an increased concentration of $O_2$ the probability of NO being oxidized to toxic $NO_2$ is correspondingly greater.

(c) Thirdly, NO reacts with superoxides to form toxic peroxynitrites, powerful oxidants capable of oxidizing lipoproteins and responsible, as are both NO and $NO_2$, for nitration of tyrosine residues. Peroxynitrite reacts nucleophilically with carbon dioxide, which is present at about 1 mM concentrations in physiological tissues, to form the nitrosoperoxycarbonate radical. This, in turn, degrades to form carbonate radical and $NO_2$, both of which are believed to be responsible for causing peroxynitrite-related cellular damage. Nitrotyrosine is used as an indicator of NO-dependent nitrative stress induced in many disease states, generally being absent or undetected in healthy subjects.

Since, in the presence of oxygen, the NO concentration determines the production rate of $NO_2$, over-delivery of NO will generate excessive quantities of toxic $NO_2$. Even if inhaled for only a short period, excess NO may form sufficient methaemoglobin to reduce oxygen delivery to the tissues to dangerously low levels, particularly in patients suffering from lung disease. Excess inert carrier gas accompanying administration of IgNO may deplete oxygen content of respiratory gas supply. On the other hand, under-administration of IgNO to patients requiring relaxation of the smooth muscles in pulmonary arteries may result in excessively high arterial blood pressures causing a low partial pressure of $O_2$ in alveolar blood (low $P_AO_2$). Consequently, precise control of the NO dosage is required at all times during administration of IgNO, in spite of irregular patient breathing patterns, fluctuations in ambient temperature and pressure, and depletion of the gas reservoir.

IgNO may be used to relax smooth muscle control of pulmonary arteriole diameter, for treating pulmonary hypertension in diseases such as acute respiratory distress syndrome (ARDS), in which impaired gas exchange and systemic release of inflammatory mediators ('acute phase proteins' and cytokines, particularly interleukins) cause fever and localised or systemic increases in blood pressure. IgNO will also relax smooth muscle control of bronchiole diameter, for treating emphysema in cases of ARDS and chronic obstructive pulmonary disease (COPD), in which the lower respiratory tract (particularly the lung parenchyma: alveoli and bronchioles) become inflamed. In COPD airways in the lower respiratory tract narrow and lung tissue breaks down, with associated loss of airflow and lung function which is not responsive to standard bronchodilating medication. IgNO administration may therefore assist in countering the 'pulmonary shunt', in which respiratory disease causes deregulation of the matching of the flow of air to the alveoli with the blood flow to the capillaries, which under normal conditions allows oxygen and carbon dioxide to diffuse evenly between blood and air (see WO 95/10315 A1).

IgNO is an effective microbicidal molecule and provides the advantage for treating infections of the respiratory tract that it acts directly in situ, whereas parenteral administration of drugs requires a high dosage to address systemic dilution and hepatic catabolism. Thus, NO has been shown to be an effective agent for killing *Mycobacterium tuberculosis* within cysts or tuberculi in a patient's lungs (see WO 00/30659 A1). IgNO may also be administered to treat pneumonia: pulmonary infection and inflammation (see WO 00/30659 A1). Pneumonia, which may accompany other respiratory or non-respiratory disease, is an inflammatory condition of the lung primarily affecting the alveoli resulting from infection with bacteria and/or viruses, less commonly by other organisms such as fungi or parasites. Bacteria generally enter the upper respiratory tract through aspiration of small quantities of microbial cells present in the nose or throat (particularly during sleep), or via airborne droplets. Systemic sepsis or septicaemia may also result in bacterial invasion of the lungs. Viral infection may occur through inhalation or distribution from the blood; in the lungs cells lining the airways, alveoli and parenchyma are damaged, and may render the patient more susceptible to bacterial infection of the respiratory tract. Response by the immune system to a respiratory tract infection may cause further damage through inflammation, particularly if the infection and the corresponding inflammation affect the lower respiratory tract. Macrophages and neutrophils located between pulmonary cells are mobilized to engulf and inactivate invading bacteria. The neutrophils also release cytokines, stimulating the immune response further. Fluid from surrounding blood vessels and from damaged cells, and containing defensive monocytes and invasive bacteria, flows into the alveoli in affected parts of the lung, thereby restricting influx of respiratory gas to the affected alveoli and reducing gas exchange efficiency, potentially causing a 'pulmonary shunt'.

Cystic Fibrosis or mucoviscidosis, ('CF') is an autosomal recessive disorder that critically affects the lungs, but also the pancreas, liver and intestine. CF generally arises from a frameshift mutation in the gene encoding the cystic fibrosis transmembrane conductance regulator (CFTR) in ciliated epithelial cells. The CFTR protein is inactivated, causing abnormal transport of sodium and chloride ions across the affected epithelia, so that secretions throughout the respiratory, alimentary and urogenital tracts become abnormally viscous. Inflammation, scarring and cyst formation occur in the pancreas due to reduced ability to mobilize the pancreatic secretions having increased viscosity. The inability of epithelial cilia to move the abnormally viscous secretions outwards for expulsion from the body causes repeated and persistent lung infections with associated chronic inflammation, pneumonia and injury to the lungs; sinus infections and infertility may also occur. Structural changes to the lungs and major airways ultimately result from the repeated infections, accompanied by hypoxia, pulmonary hypertension, respiratory failure and heart failure. The three most common bacterial lung infections in CF patients are *Staphyococcus aureus, Haemohilus influenzae* and *Pseudomonas aeruginosa*. Breathing difficulties are often aggravated by allergic bronchopulmonary aspergillosis ('ABPA') arising from infection with *Aspergillus fumigatus*, or other filamentous fungi. Mycobacterial infections of the lungs are also frequently associated with CF. Chronic administration of antibiotic and corticosteroid therapies provides conditions selecting for resistant bacterial and fungal growth, while the defective mucociliary clearance may serve to protect bacterial and fungal infection from both endogenous defence mechanisms and exogenous therapies.

Damage to the pancreas arising from CF may result in a reduction of insulin-synthesizing capacity through loss of islet cells and development of CF related diabetes ('CFRD'). Liver disease resulting from increased viscosity of bile is a further CF complication, which may result in cirrhosis and loss of functions such as toxin catabolism and synthesis of blood clotting proteins. Children suffering from CF grow poorly due to reduced nutrient absorption through the viscous mucus of the alimentary tract and from the effects of chronic infection. In CF the alimentary tract is particularly poor at absorbing Vitamin K, causing a potential reduction in the blood clotting rate of CF patients to dangerous levels.

A number of complications are commonly associated with respiratory disease, yet have the potential to be ameliorated by administration of IgNO. In respiratory disease the bronchioles and alveoli may become obstructed or constricted by smooth muscle contraction or inflammation. Reduced access of respired gas to constricted bronchioles and alveoli reduces exchange of oxygen and $CO_2$ between the respiratory gas and the pulmonary blood supply. In lung diseases such as asthma, pneumonia, bronchitis and emphysema, the lungs' small peripheral arteries—the pulmonary arteries—constrict under conditions in which the oxygen tension falls, causing pulmonary hypertension. In primary pulmonary hypertension the increase in resistance to the flow of blood through the pulmonary arteries and capillaries may be sufficient to cause the heart's right ventricle to fail. A further potential complication is dysregulation of the flow of air to the alveoli which is normally matched to the blood flow to the capillaries, allowing oxygen and carbon dioxide to diffuse evenly between blood and air (see WO 95/10315 A1). This uncoupling of smooth muscle regulation of the respective diameters of the airways in the lungs and of the pulmonary capillaries results in a "pulmonary shunt": the supply of respiratory gas is no longer controlled in proportion to the blood flow through the capillaries in the affected part of the lungs. The result is normal perfusion with blood while the supply of air is restricted. Lower $O_2$ concentrations in the blood and tissues, and especially higher $CO_2$ concentrations, increase the pulse rate, placing more stress on the heart, which may already be compensating for pulmonary hypertension. Applying an increase in the pressure of supplied respiratory gas, as in CPAP may assist in reducing influx of fluid into the alveoli in cases of pulmonary inflammation, may assist in transfer of oxygen from respiratory gas into the blood-stream. However, where the increased pressure of the respiratory gas supply is inadequate to improve oxygen exchange either generally or in particular regions of an affected lung, any 'compensatory' increase in pulmonary hypertension may worsen the prognosis.

The surface barriers of the nose, mouth and the mucus secreted into the respiratory tract aid in protection of the tract against infection. However, inhibition of mucus expulsion by reduced movement of the cilia of the epithelial cells at the surface of the respiratory tract or by thickening of the mucus, as in cystic fibrosis, may result in infection occurring within the mucus itself. The innate immune response to infection includes inflammation, with longer term protection being provided against repeat infection by the cell-mediated and humoral components of the adaptive immune system. Although macrophages provide the primary cellular defence against infection macrophages themselves may undergo parasitic infection by fungal, bacterial and viral infections which may then result in disruption of the immune response to infectious agents (e.g.; due to impairment of antigen presentation) and further distribution of the infection.

Endogenously produced NO is partially responsible for the cytotoxic actions of macrophages. The mechanisms discussed above relating to potential cell damaging activities of NO supplied either endogenously or exogenously, such as the production of superoxide, the nitration of tyrosine residues in critical proteins, and the stable binding to haem groups by NO to inhibit electron transport pathways and energy metabolism, are all mechanisms which will also apply to the activity of NO in countering infection. NO being an effective microbicidal molecule, IgNO offers the advantage for treating infections of the respiratory tract that it acts directly in situ, whereas parenteral administration of drugs requires a high dosage to address systemic dilution and hepatic catabolism.

Furthermore, NO reduces the abnormally high viscosity of mucus occurring in the lower respiratory tract of CF patients, allowing ciliary activity to be restored and excess mucus to be rapidly cleared from the respiratory tract (see U.S. Pat. No. 8,518,457 B2). Thus, a combination of IgNO administration with CPAP provides an opportunity for the increased pressure of respiratory gas to counteract the reduced efficiency of gas exchange under conditions of pulmonary inflammation, where the IgNO counteracts the pulmonary shunt by relaxing smooth muscle control of bronchioles and arterioles to cause dilation of these airways and blood vessels. Thus, each of the two aspects of this treatment employing IgNO+CPAP enhances the therapeutic effect of the other, resulting in an unexpectedly effective treatment. Additionally, IgNO provides the microbicidal activity of NO for treating infections located in the lower respiratory tract, which may be a cause of or an accompaniment to the respiratory disease requiring treatment.

Miller et al., Gaseous nitric oxide bacterial activity retained during intermittent high-dose short duration exposure, Nitric Oxide 20 (2009) 16-23 describe the use of nitric oxide as an anti-infective agent for non-healing wounds due to its non-specific antimicrobial properties.

Using gaseous nitric oxide as an inhalable medicament for the treatment of reversible pulmonary vasoconstriction or bronchus constriction is known. Nitric oxide is usually administered to mammals suspected of having acute pulmonary vasoconstriction at a concentration of from 1 ppm to 40 ppm in air, pure oxygen or another suitable gas or gas mixture for as long as needed. This is disclosed, for example, in EP 0 560 928 B1.

Nitric oxide is also known as a mucolytic agent wherein the nitric oxide is provided in concentrations of about 160 ppm to about 220 ppm to the breathing gas, for example air. This is disclosed, for example, in U.S. Pat. No. 8,518,457 B2.

A controlled gas supply system for supplying nitric oxide to the breathing air to a patient is known from EP 0 973 443 B1.

Furthermore, in order to recruit additional lung units for the gas exchange it is known to use a positive airway pressure (CPAP) device, mainly in order to treat obstructive sleep apnea.

Christian Putensen et al: Positive airway pressure modulates effect of a nitric oxide on the ventilation perfusion distributions in canine lung injury, Chest, 106, 5, Nov. 1994, page 1563 to 1569, suggest using a combination of the application of positive airway pressure and the inhalation of nitric oxide in concentrations ranging from 5 to 80 ppm to cause selective pulmonary vasodilation and to improve pulmonary gas exchange in patients with acute lung injury.

SUMMARY OF THE INVENTION

It is an object of the present invention to provide a medicament and a device for the treatment of, treatment of complications arising from, and/or prevention of respiratory disorders caused by bacterial, viral, protozoal, fungal and/or microbial infections, preferably for the treatment of complications arising from cystic fibrosis.

In a first aspect, use of gaseous nitric oxide for the production of an inhalable medicament for the treatment of, treatment of complications arising from, and/or prevention of respiratory disorders caused by bacterial, viral, protozoal, fungal and/or microbial infections in a mammal under positive airway pressure is suggested.

It has been found that the effect on bacteria, viruses, protozoae, fungi and/or microbes in infections of the lungs or upper airways is increased by the application of positive airway pressure.

It has also been found that the use of gaseous nitric oxide for the production of an inhalable medicament for the treatment of complications arising from cystic fibroses in a mammal under positive airway pressure provides superior results of the mucolytic properties of the nitric oxide in particular as the nitric oxide can reach regions of the lungs which could not be reached when using a different pressure regime.

Positive airway pressure is preferably achieved by non invasive ventilation (NIV) methods and devices such as continuous positive airway pressure (CPAP) or bilevel positive airway pressure (BiPAP).

Continuous positive airway pressure (CPAP) is the use of positive airway pressure to maintain a continuous level of positive airway pressure in a spontaneously breathing patient. The ventilator does not cycle during CPAP, no additional pressure above the level is provided, and patients must initiate all of their breaths.

Bilevel positive airway pressure (BiPAP) is a continuous positive airway pressure (CPAP) mode used during noninvasive positive pressure ventilation (NIV). It delivers a preset inspiratory positive airway pressure and expiratory positive airway pressure. BiPAP can be described as a continuous positive airway pressure system with a time-cycled or flow-cycled change of the applied CPAP level.

Preferably nitric oxide is present in the inhalable medicament with a concentration of between 40 ppm and 1000 ppm, preferably between 80 ppm and 220 ppm or between 140 ppm and 220 ppm in order to achieve the highest possible impact.

It has also been found that preferably said disorder to be treated could be selected from the group consisting of: a ventilator associated pneumonia (VAP), a toxoplasmosis, a heparin-protamine reaction, a traumatic injury, a traumatic injury to the respiratory tract, acidosis or sepsis, acute mountain sickness, acute pulmonary edema, acute pulmonary hypertension, acute pulmonary thromboembolism, adult respiratory distress syndrome, an acute pulmonary vasoconstriction, aspiration or inhalation injury or poisoning, asthma or status asthmaticus, bronchopulmonary dysplasia, hypoxia or chronic hypoxia, chronic pulmonary hypertension, chronic pulmonary thromboembolism, cystic fibrosis (CF), fat embolism of the lung, haline membrane disease, idiopathic or primary pulmonary hypertension, inflammation of the lung, perinatal aspiration syndrome, persistent pulmonary hypertension of a newborn, post cardiac surgery, a bacterial-, viral- and/or fungal bronchiolitis, a bacterial-, viral- and/or fungal pharyngitis and/or laryngotracheitis, a bacterial-, viral- and/or fungal pneumonia, a bacterial-, viral- and/or fungal sinusitis, a bacterial-, viral- and/or fungal upper and/or lower respiratory tract infection, a bacterial-, viral- and/or fungal-exacerbated asthma, a respiratory syncytial viral infection, bronchiectasis, bronchitis, chronic obstructive lung disease (COPD), cystic fibrosis (CF), emphysema, otitis, otitis media, primary ciliary dyskinesia (PCD), and pulmonary aspergillosis (ABPA) and cryptococcosis.

In another aspect, a method of providing an inhalable medicament by injecting nitric oxide in a concentration of between 40 ppm and 1000 ppm, preferably between 80 ppm and 220 ppm or between 140 ppm and 220 ppm, to the breathing gas of a positive airway pressure device is suggested.

In order to provide to the patient a suitable concentration of nitric oxide which can be administered to specific areas of the lung, the nitric oxide is preferably injected in a single pulse, in multiple subsequent pulses of equal or varying width, or as a constant flow with a varying or fixed flow rate.

Preferably, the nitric oxide is injected into a flow of breathing gas which is provided under positive airway pressure and the nitric oxide is injected together with a carrier gas such that the gas injected is already in the correct concentration.

In order to ensure that the nitric oxide is injected into the breathing gas of the positive airway pressure device only when the patient is inhaling, it is preferably injected only when a predetermined breathing gas flow rate is exceeded or if the pressure in a patient interface falls below a predetermined pressure.

If the concentration of the carrier gas is high, it might be necessary to inject additional oxygen into the flow of breathing gas in order to supply to the patient a breathable gas with a suitable concentration of oxygen.

To find a balance between the positive and negative characteristics of nitric oxide, the nitric oxide is preferably injected into the breathing gas of the positive airway pressure device during an interval of between 1 minute and 60 minutes, preferably between 15 minutes and 30 minutes, with an interval every second day up to 5 intervals a day.

In another aspect a gaseous mixture consisting of breathing gas and nitric oxide in a concentration of between 40 ppm and 1000 ppm, preferably between 80 ppm and 220 ppm or between 140 ppm and 220 ppm for use in a method of treating respiratory disorders caused by bacterial, viral, protozoal, fungal and/or microbial infections in a mammal under positive airway pressure is suggested.

In yet another aspect a gaseous mixture consisting of breathing gas and nitric oxide in a concentration of between 40 ppm and 1000 ppm, preferably between 80 ppm and 220 ppm or between 140 ppm and 220 ppm for use in a method of treating complications arising from cystic fibrosis in a mammal under positive airway pressure is suggested.

Yet another suggestion is the provision of a gaseous mixture consisting of breathing gas and nitric oxide in a concentration of between 40 ppm and 1000 ppm, preferably between 80 ppm and 220 ppm or between 140 ppm and 220 ppm for use in a method of treating, treating complications arising from, and/or preventing a disorder selected from the group consisting of: a ventilator associated pneumonia (VAP), a toxoplasmosis, a heparin-protamine reaction, a traumatic injury, a traumatic injury to the respiratory tract, acidosis or sepsis, acute mountain sickness, acute pulmonary edema, acute pulmonary hypertension, acute pulmonary thromboembolism, adult respiratory distress syndrome, an acute pulmonary vasoconstriction, aspiration or inhalation injury or poisoning, asthma or status asthmaticus, bronchopulmonary dysplasia, hypoxia or chronic hypoxia, chronic pulmonary hypertension, chronic pulmonary thromboembolism, cystic fibrosis (CF), fat embolism of the lung, haline membrane disease, idiopathic or primary pulmonary hypertension, inflammation of the lung, perinatal aspiration syndrome, persistent pulmonary hypertension of a newborn, post cardiac surgery, a bacterial-, viral- and/or fungal bronchiolitis, a bacterial-, viral- and/or fungal pharyngitis and/or laryngotracheitis, a bacterial-, viral- and/or fungal pneumonia, a bacterial-, viral- and/or fungal sinusitis, a bacterial-, viral- and/or fungal upper and/or lower respiratory tract infection, a bacterial-, viral- and/or fungal-exacerbated asthma, a respiratory syncytial viral infection, bronchiectasis, bronchitis, chronic obstructive lung disease (COPD), cystic fibrosis (CF), emphysema, otitis, otitis media, primary ciliary dyskinesia (PCD), and pulmonary aspergillosis (ABPA) and cryptococcosis.

To be in a position to apply nitric oxide under positive airway pressure to a patient, the following device for the treatment of, treatment of complications arising from, and/or prevention of respiratory disorders caused by bacterial, viral, protozoal, fungal and/or microbial infections is suggested, preferably for the treatment of complications arising from cystic fibrosis, including a positive airway pressure device for providing a breathing gas under a positive airway pressure to a patient interface, a source of nitric oxide for providing gaseous nitric oxide, a gas injector for injecting nitric oxide provided by the source of nitric oxide into the breathing gas provided by the positive airway pressure device under positive pressure, a flow rate sensor for sensing the flow rate of the breathing gas provided to the patient interface under positive airway pressure, and a controller programmed for controlling the gas injector for injecting the nitric oxide to the breathing gas provided by the positive airway pressure device when a flow rate detected by the flow rate sensor exceeds a predetermined threshold flow rate.

The combination of the nitric oxide injector, the flow rate sensor and the positive airway pressure device enables the treatment of a patient under positive airway pressure with nitric oxide.

The patient interface may have any form which is suitable to supply a patient with a positive airway pressure. Accordingly, the patient interface may be a nasal mask, a face mask, a full face mask, a nasal cannula, a cannula or any other known mask or device to supply a positive airway pressure to a patient.

The flow rate sensor may situated in any position which enables the flow rate sensor to measure the flow of gas towards the patient reliably. In particular, the flow rate sensor may be situated in the patient interface, particularly a mask, in the hose or in the positive airway pressure device.

Preferably, the controller is programmed to control the gas injector to inject the nitric oxide in a single pulse, in two pulses or in multiple subsequent pulses of equal or varying width, or as a constant flow with a varying or fixed flow rate.

It is also preferred if the controller is programmed to control the gas injector to inject the nitric oxide such that a concentration of nitric oxide in the breathing gas of between 40 ppm and 1000 ppm, preferably between 80 ppm and 220 ppm or between 140 ppm and 220 ppm is achieved.

Preferably, the controller is programmed to determine the onset of inspiration of a patient and to control the injection of the nitric oxide into the breathing gas on this basis or after a predetermined delay.

In order to meet the prescriptions, the controller is preferably programmed to control the injection of the nitric oxide into the breathing gas of the positive airway pressure device during an interval of between 1 minute to 60 minutes, preferably between 15 minutes and 30 minutes, with an interval every second day up to 5 intervals a day.

By the same token, it is preferred if the controller is programmed to control the positive airway pressure device and the gas injector to provide the breathing gas under positive airway pressure without the nitric oxide between the intervals.

To be in a position to analyse the gas in the patient interface, preferably a gas sensor for determining the concentration of nitric oxide, oxygen and/or nitrogen dioxide in the patient interface is present and the gas sensor is connected to the controller to adjust the concentration of nitric oxide injected.

In a preferred embodiment, the patient interface comprises a purging means for purging the patient interface with a purging gas in order to remove residual nitric oxide and/or nitrogen dioxide from the patient mask.

The combination of gaseous nitric oxide and the provision of positive airway pressure increases the effect on bacteria, viruses, protozoe, fungi, and/or microbes in infections of the lungs or upper airways.

In particular, it has been found that the use of gaseous nitric oxide for the production of an inhalable medicament for the treatment of cystic fibroses in a mammal under positive airway pressure provides superior results of the treatment and of the mucolytic properties of the nitric oxide in particular as the nitric oxide can reach regions of the lungs which could not be reached when using a different pressure regime.

Depending on the desired distribution of the nitric oxide in the lung, the nitric oxide could be injected in a single pulse or in multiple subsequent pulses such that different areas of the lung can be reached by the nitric oxide.

In order to make sure that nitric oxide does not reside, for example, in the mouth of the patient, the nitric oxide is preferably injected into the breathing gas of the positive airway pressure device only when a predetermined breathing gas flow is exceeded. In other words, only if the patient inhales, the inhalable medicament is provided by injecting the nitric oxide into the breathing gas of the positive airway pressure device.

When exposed to oxygen, nitric oxide is unstable and undergoes continuous oxidation to nitrogen dioxide and higher oxides of nitrogen. These higher nitrogen oxides are toxic to the lung. Furthermore, nitric oxide reacts with oxygen water to form nitrogen dioxide or nitrous acid. Accordingly, it is not desired to provide nitrous oxide in large concentrations to the watery environment in the mouth of a patient for too long because nitrous acid would be formed in this connection.

By the provision of this device, a reliable and secure administration of nitric oxide to a patient can be achieved, which avoids the residence of nitric oxide in the watery environment in the mouth of the patient while, at the same time, providing a positive airway pressure which recruits additional lung units for the gas exchange and thus improves the quality of the therapy versus the administration of nitric oxide to a patient under ambient pressure.

It is also preferred if the controller is programmed to control the positive airway pressure device and the gas injector to provide the breathing gas under positive airway pressure without providing the nitric oxide between the intervals.

BRIEF DESCRIPTION OF THE DRAWINGS

The present disclosure will be more readily appreciated by reference to the following detailed description when being considered in connection with the accompanying drawings in which.

DETAILED DESCRIPTION OF PREFERRED EMBODIMENTS

In the following, the invention will be explained in more detail with reference to the accompanying Figures. In the Figures, like elements are denoted by identical reference numerals and repeated description thereof may be omitted in order to avoid redundancies.

Figure 1:
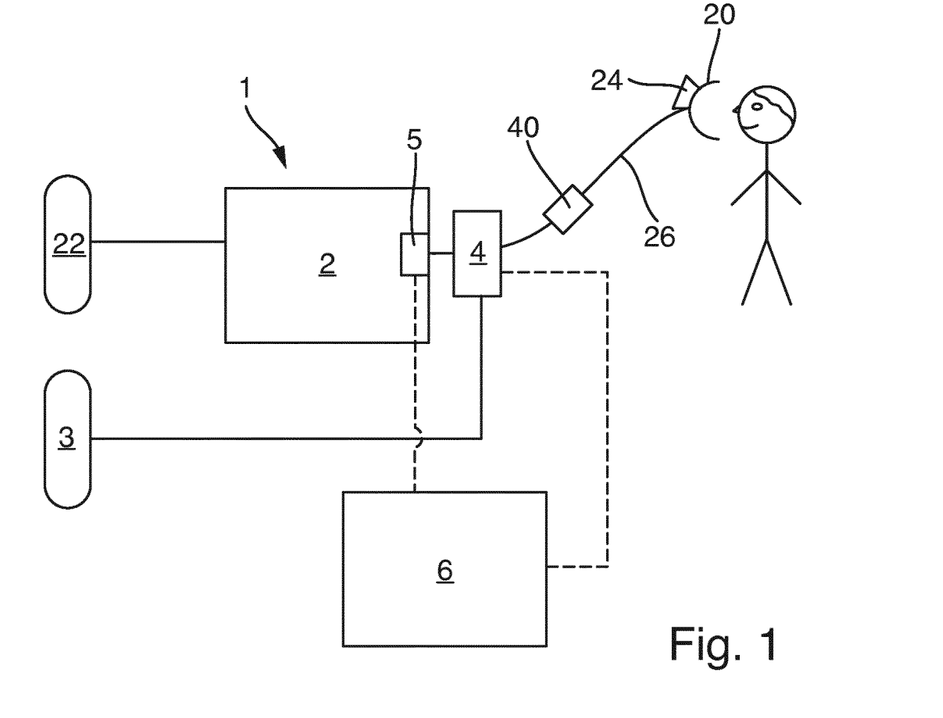
FIG. 1 is a schematic view of a device for the treatment of respiratory disorders.

In FIG. 1 a device 1 for the treatment of, treatment of complications arising from, and/or prevention of respiratory disorders caused by bacterial, viral, protozoal, fungal and/or microbial infections, preferably for the treatment of complications arising from cystic fibrosis is schematically shown.

The disorders to be treated by means of the device 1 are preferably selected from the group consisting of: a ventilator associated pneumonia (VAP), a toxoplasmosis, a heparin-protamine reaction, a traumatic injury, a traumatic injury to the respiratory tract, acidosis or sepsis, acute mountain sickness, acute pulmonary edema, acute pulmonary hypertension, acute pulmonary thromboembolism, adult respiratory distress syndrome, an acute pulmonary vasoconstriction, aspiration or inhalation injury or poisoning, asthma or status asthmaticus, bronchopulmonary dysplasia, hypoxia or chronic hypoxia, chronic pulmonary hypertension, chronic pulmonary thromboembolism, cystic fibrosis (CF), fat embolism of the lung, haline membrane disease, idiopathic or primary pulmonary hypertension, inflammation of the lung, perinatal aspiration syndrome, persistent pulmonary hypertension of a newborn, post cardiac surgery, a bacterial-, viral- and/or fungal bronchiolitis, a bacterial-, viral- and/or fungal pharyngitis and/or laryngotracheitis, a bacterial-, viral- and/or fungal pneumonia, a bacterial-, viral- and/or fungal sinusitis, a bacterial-, viral- and/or fungal upper and/or lower respiratory tract infection, a bacterial-, viral- and/or fungal-exacerbated asthma, a respiratory syncytial viral infection, bronchiectasis, bronchitis, chronic obstructive lung disease (COPD), cystic fibrosis (CF), emphysema, otitis, otitis media, primary ciliary dyskinesia (PCD), and pulmonary aspergillosis (ABPA) and cryptococcosis.

The device 1 includes a positive airway pressure device 2 for providing a breathing gas under positive airway pressure to a patient. In the present example, the positive airway pressure device 2 is provided as a CPAP device. The breathing gas is delivered via a hose 26 to a patient interface 20 which is shown exemplary as a CPAP mask. Typically, a full face patient mask which fits over nose and mouth of the patient to be treated is used as the patient interface 20.

However, the positive airway pressure device 2 could be provided in a different setup such as a BiPAP or any other device which provides a positive airway pressure to a patient in a noninvasive ventilation setup allowing the patient to breathe spontaneously.

The patient interface 20 may have any form which is suitable to supply a patient with a positive airway pressure. Accordingly, the patient interface 20 may be a nasal mask, a face mask, a full face mask, a nasal cannula, a cannula or any other known mask or device to supply a positive airway pressure to a patient.

The positive airway pressure device 2 provides to the patient a breathing gas in the form of either ambient air, medical air or any other breathable gas mixture provided by a source of breathing gas 22 under positive pressure. The principle of the provision of a breathing gas to a patient under positive airway pressure in order to achieve in the patient a positive airway pressure is generally known.

The positive airway pressure device 2 blows breathing gas at a prescribed positive pressure through the hose 26 to the patient interface 20. In the gas path between the positive airway pressure device 2 and the patient interface 20 a positive airway pressure is build up and maintained. In common continuous positive airway pressure (CPAP) devices 2 the pressure is usually measured in centimetres of water ($cmH_2O$). A typical CPAP machine can deliver pressures between 4 and 20 $cmH_2O$. More specialised units can deliver pressures up to 25 or 30 $cmH_2O$.

Furthermore, a source of gaseous nitric oxide 3 is provided. The source of gaseous nitric oxide 3 is connected to a gas injector 4 which is arranged for injecting nitric oxide provided by the source of gaseous nitric oxide 3 to the breathing gas pressurized by the positive airway pressure device 2 and conducted via the hose 26. The gas injector 4 can be situated at the hose 26 close to the positive airway pressure device 2 or close to the patient interface 20. It is preferred that the gas injector 4 is situated close to the patient interface 20 or even at the patient interface 20 in order to be in a position to control the injection of the nitric oxide precisely and to avoid residual nitric oxide in the hose 26 at undesired phases of the breathing cycle.

A flow rate sensor 5 is present which can be situated in the positive airway pressure device 2 or at any other position along the breathing gas path. The flow rate sensor 4 senses the flow rate of the breathing gas provided by the positive airway pressure device 2. The flow rate sensor 5 can determine the flow rate directly or indirectly, for example by measuring a pressure drop in the hose 26 and calculating the flow rate on this basis.

Figure 2:
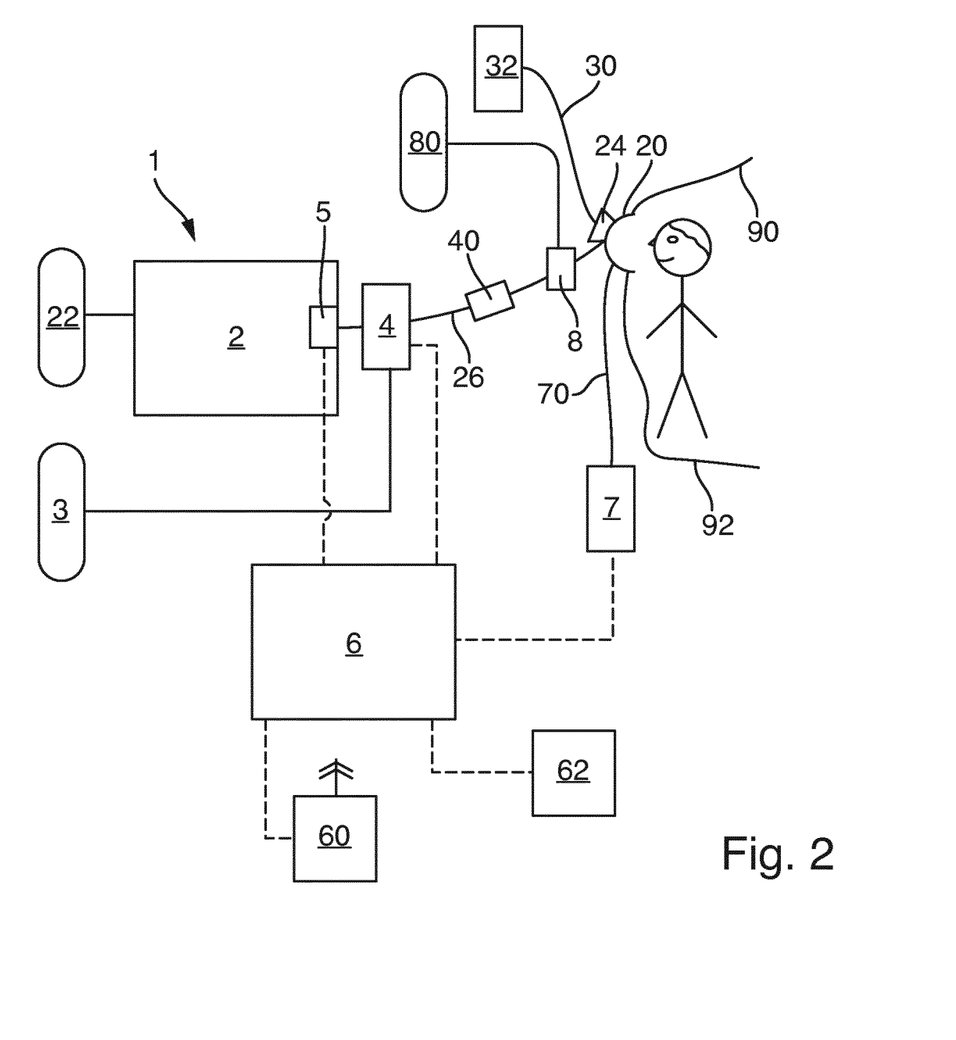
FIG. 2 is a schematic view of another device for the treatment of respiratory disorders.

The flow rate sensor 5 may also be situated in a position different from the position shown in the Figures. In particular, the flow rate sensor 5 may be situated in the patient interface 20, particularly a mask, or in the hose 26.

Accordingly, the flow rate sensor 5 determines a positive flow of breathing gas once the patient inhales. When the patient exhales, a pressure relief valve 24 or any other suitable exhaust opening situated in the patient interface 20 releases the exhaled breathing gas of the patient to the outside. Accordingly, when the patient exhales, the flow rate sensor 5 does not sense any positive gas flow as, due to the positive airway pressure provided by the positive airway pressure device 2 to the patient interface 20, a flow of fresh breathing gas towards the patient interface 20 from the positive airway pressure device 2 cannot take place. Due to the pressure relief valve 24 or any other suitable exhaust opening, the flow rate sensor 5 will also not measure a negative flow of breathing gas when the patient is exhaling.

Figure 3:
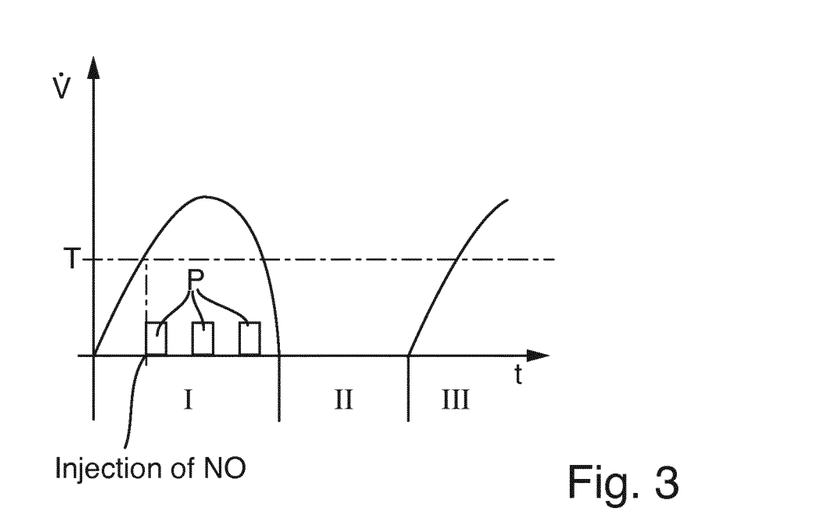
FIG. 3 is a schematic diagram showing the breathing cycle in a device.

Accordingly, as schematically shown in FIG. 3, the flow rate sensor 5 measures a positive gas flow from the positive airway pressure device 2 towards the patient interface 20 when the patient inhales. This is schematically shown in inhalation phase I in FIG. 3.

In exhalation phase II the patient exhales such that a flow of breathing gas cannot be detected by the flow rate sensor 5. Only when the patient inhales again in inhalation phase III, the flow rate sensor 5 senses a positive air flow.

A controller 6 is provided which is connected to the flow rate sensor 5 to receive the signal of the flow rate sensor 5. The controller 6 is programmed for controlling the injection of the nitric oxide into the breathing gas by means of triggering the gas injector 4. If the flow rate $\dot{V}$ detected by the flow rate sensor 5 exceeds a predetermined threshold T, the injection of nitric oxide is triggered by the controller 6.

Accordingly, nitric oxide is only injected by the gas injector 4 into the breathing gas provided under positive airway pressure if the patient inhales. By this means it can be avoided that nitric oxide remains in an area of the mouth or airways of a patient for a too long time with the possible negative effects associated therewith.

In order to treat different areas or regions within the lung of the patient, a single or a number of subsequent pulses P of nitric oxide can be injected into the positive flow of breathing gas detected by the flow rate sensor 5. By triggering the different spikes of the injection of nitric oxide, the depth within the lungs that can be reached by the nitric oxide can be varied. The different pulses may have differing widths, depending on the respective prescription.

In an alternative, the nitric oxide is injected into the breathing gas as a constant flow or varying flow of gas.

The controller 6 is programmed and arranged to control the gas injector 4 such that the concentration of the nitric oxide in the breathing gas can be controlled, preferably to a concentration of between 40 ppm and 1000 ppm, preferably between 80 ppm and 220 ppm or between 140 ppm and 220 ppm.

Preferably, the controller 6 is further programmed for controlling the injection of the nitrous oxide via the gas injector 4 only during an interval of between 1 minute and 60 minutes, preferably between 15 minutes and 30 minutes, with an interval every second day up to 5 intervals a day and automatically stops the injection of nitrous oxide after each interval. In the remainder of the time, nitric oxide is not administered to the patient but only breathing gas is provided under positive airway pressure.

The concentration of the nitric oxide as well as frequency and duration of the intervals are chosen such that bacteria, viruses, protozoae, fungi and/or microbes can be decreased effectively. Hence, a high concentration would give shorter intervals etc.

The source of gaseous nitric oxide 3 preferably provides a carrier gas, for example $N_2$, such that the nitric oxide is provided in a concentration of about 100 ppm to 10000 ppm, preferably 1000 ppm to 10000 ppm. The higher the concentration of the nitric oxide in the source of gaseous nitric oxide 3, the smaller a gas container for supplying the nitric oxide can be. This is preferred for distribution reasons.

However, in order to make sure that the patient inhales the desired concentration of nitric oxide in the breathing gas offered to the patient, the gas supplied by the source of gaseous nitric oxide needs 3 to be diluted. Furthermore, the N2 content of the gas supplied by the source of gaseous nitric oxide 3 needs to be supplemented by a suitable concentration of oxygen such that the patient does not suffer from low oxygen levels.

To provide a suitable mixture of gas which preferably comprises the oxygen content of ambient air, a supply of oxygen is provided which enables the addition of oxygen to the breathing gas which is offered under positive airway pressure to the patient.

However, the higher the concentration of nitric oxide in the source of gaseous nitric oxide 3, the lower the proportion of the carrier gas, for example nitrogen, such that it is no longer necessary to add oxygen in order to achieve a breathable gas. In other words, the carrier does not displace oxygen in an amount such that oxygen would have to be added.

In the positive airway pressure device 2 the breathing curve of the patient cannot be known beforehand because the patient breathes spontaneously. However, by means of the flow rate sensor 5 it can be determined whether the patient is actually inhaling or exhaling. Accordingly, the gas injector 4 is controlled by the controller 6 according to a predetermined scheme and preferable injects a mixture of nitric oxide and the carrier gas nitrogen upstream of a mixing channel 40 in which the gas is conducted in turbulent manner such as to ensure proper mixing.

The nitric oxide can be injected via the gas injector 4 just on the basis of the inhaled gas flow as determined by the flow rate sensor 5.

In FIG. 2 another device 1 for the treatment of, treatment of complications arising from, and/or prevention of respiratory disorders is shown which has, in principle, the same setup as the one shown in FIG. 1. Additional preferred features of the device 1 are shown therein.

In a preferred embodiment, at the patient interface 20 a sample gas conduit 70 is provided which enables drawing test samples of air from the gas that is offered to the patient under positive airway pressure. The test samples can be analysed in a gas sensor 7 such that the concentration of nitric oxide injected into the gas stream offered to the patient under positive airway pressure can be determined. The concentrations determined by the gas sensor 7 can be supplied to the controller 6 to make sure that the gas injector 4 injects the correct amount of nitric oxide such that the desired concentration is achieved at the patient interface 20 where the gas is offered to the patient under positive airway pressure.

Furthermore, via the gas sensor 7 the occurrence of nitrogen dioxide in the patient interface 20 can be monitored and if the concentration of nitrogen dioxide exceeds a predetermined level, the controller 6 lowers the concentration of nitric oxide injected into the gas flow, stops the injection of nitric oxide for one or more breathing cycles and/or triggers an alarm.

In a preferred embodiment, the gas sensor 7 also allows measuring the oxygen content of the gas offered to the patient under positive airway pressure and adjusts the injection of additional oxygen supplied by an oxygen supply 80 via an oxygen injector 8 into the breathing gas of the patient accordingly. The oxygen concentration offered to the patient under positive airway pressure preferably resembles the oxygen concentration in ambient air, but can also be higher if the prescription calls for a higher concentration of oxygen.

The injection of oxygen into the flow of breathing gas takes place as close as possible to the patient interface 20 in order to reduce the contact of the oxygen with the nitric oxide to the least possible degree.

In one preferred embodiment, the nitric oxide in combination with the carrier gas—for example N2—is mixed with oxygen and/or ambient air before it is injected into the hose 26 for delivering the gas to the patient interface 20 such that the gas injected into the hose 26 already comprises the desired concentration of nitric oxide as well as oxygen. The gas is provided in a volume which displaces the gas in the hose 26. In other words a "packet" of gas is provided to the hose 26 which is inhaled by the patient as a whole, without any further mixing with the air provided by the positive airway pressure device 2.

The gas packet can be injected as a spike into the gas flow inhaled by the patient and is provided to the hose 26 under the same pressure or slight overpressure relative to the positive airway pressure provided by the positive airway pressure device 2. The gas packet moves along the hose 26, into the patient interface 20 and then into the lungs of the patient such that in the lungs a concentration layering can be obtained in which at certain layers a high concentration of nitric oxide is present.

The controller 6 is preferably connected to a data communication module 60 as well as a compliance module 62 which enables recording of the treatment data such that a doctor or treatment centre in a hospital can determine whether the patient was compliant and conducted the treatment in the prescribed manner. The data communication module 60 can use any suitable form of communication with a doctor or treatment centre such as, for example, wired data communication, wireless data communication or storage of data to a suitable data carrier. The format of the data communication preferably uses standard communication formats and protocols such as the internet protocol or any other telecommunication standards which enable communication of data between the device 1 and the doctor or treatment centre.

The compliance module 62 may record the operation of the device 1 over a certain time period, for example a day, a week or between consultations and can, upon establishing a data connection via the data communication module 60, send the data for analysis to the doctor or treatment centre. If the doctor or treatment centre discovers that the prescription should be changed or adjusted, the doctor or treatment centre can either communicate the new prescription data to the controller 6 of the device 1 or can require the patient to make an appointment with the doctor or treatment centre.

If the device 1, the controller 6 and/or the compliance monitor 60 discovers an alarm condition, for example if the concentrations of nitric oxide or nitrogen dioxide in the exhaled gas exceed a certain threshold, a connection is established immediately by the data communication module 60 and the doctor or treatment centre is informed of the alarm condition such that measures could be taken.

In an alternative, an online connection is established between the data communication module 60 and the doctor or treatment centre and the compliance module 62 transmits the data in real time or with a minor delay. In such an arrangement, the doctor or treatment centre can monitor the treatment such that immediate feedback of the doctor or the treatment center can be provided and/or the prescription can be changed or modified as to the progress of the treatment. Accordingly, it is possible that the treatment is adjusted online by the doctor or treatment center, for example by adjusting the concentration of nitric oxide and/or oxygen supplied to the patient, the duration of a single treatment session as well as number of treatments a day.

The occurrence of nitrogen dioxide in the patient interface 20 is undesirable because nitrogen dioxide is a toxic gas. Nitric oxide, however, is rapidly oxidized in air to nitrogen dioxide such that the treatment of the patient with nitric oxide in combination with the necessity of providing oxygen to the patient either via ambient air with an oxygen content of about 21% or via a specific gas mixture, e.g. of the nitric oxide in combination with its carrier gas (e.g. nitrogen) and added oxygen in a prescribed concentration.

In order to remove residues of nitric oxide or nitrogen dioxide from the patient interface 20 preferably a constant flow of a purging gas is supplied. The purging gas can be provided by means of the hose 26 and can thus consist of the breathing gas which is offered to the patient interface 20 under positive airway pressure. In an alternative or as a complement, the purging gas can also be supplied to the patient interface 20 via a separate purging input line 90 which preferably supplies air or any other breathable gas mixture to the patient interface 20. In order to provide a constant flow of purging gas through the patient interface 20, the purging gas is constantly removed from the patient interface 20 by means of a purging output line 92 which withdraws the gas.

The purging gas can also be withdrawn from the patient interface 20 via the sample gas conduit 70 such that the constant flow of purging gas through the patient interface 20 can be established by sampling the gas which is intended to be analyzed in the gas sensor 7. In order to provide for this constant gas flow, the sample gas conduit 70 for drawing gas samples could be used and a constant gas flow can be withdrawn from the patient interface 20 at desired positions of the mask.

In order to provide for the positive airway pressure in the patient interface 20, the sample gas conduit 70 and/or the purging output line 92 preferably provides for a flow resistance or an pressure relief valve which enables the positive airway pressure in the patient interface 20 to be maintained at the desired positive airway pressure level.

However, as the regions of the patient interface which are not properly vented in a breathing cycle are not the most preferred regions in the patient interface 20 to take samples for the analysis of the gas provided to the patient under positive airway pressure, it is preferred to have separate sample gas conduit 70 and purging lines 90, 92.

The purging lines 90, 92 could be specifically be attached to the patient interface 20 in a region in which the ventilation of the patient interface 20 is poor such as in the regions of the nose-piece above the nostrils. As an alternative, the purge input line 90 can be connected to this region of the patient interface 20 in order to provide a constant purging gas flow out of the regions of poor ventilation of the patient interface 20.

As yet another alternative, the pressure relief valve 24 in the patient interface 20 through which the gas exhaled by the patient is discarded could also be used for purging the patient interface 20. To this end the pressure supplied to the patient interface 20 by means of the positive airway pressure device 2 is set to a level which exceeds the level of set pressure of the pressure relief valve 24 such that a constant outflow of gas though the pressure relief valve 24 is achieved, at least as long as the patient is not inhaling. Due to the constant flow of gas though the pressure relief valve 24 the patient interface 20 is constantly purged.

In the embodiments discussed above the removal of nitric oxide and/or nitrogen dioxide which is resident in the patient interface 20 after exhaling, due to an erroneous injection of nitric oxide or due to an excess concentration of nitric oxide, can be facilitated such that the constant flow of the purging gas removes unwanted concentrations of nitric oxide and/or nitrogen dioxide.

Nitric oxide and nitrogen dioxide which is exhaled as well as the nitric oxide and nitrogen dioxide which is withdrawn, for example via the purging gas, from the patient interface 20 can be treated before it is released to the environment. For the treatment of nitric oxide and nitrogen dioxide different methods and devices are available. However, in a regular setting the exhaled gas as well as the purging gas withdrawn from the patient interface 20 will be released into the surroundings without prior treatment because the overall concentrations of these gases are very low.

However, in case the gas exhaled by the patient as well as the gas withdrawn from the patient interface 20 is to be treated, the gases are collected in a centralized waste gas treatment device 32 which treats the NO and nitrogen dioxide such that the treated gas can be released to the outside. In hospitals such devices for waste gas treatment are usually present.

In order to provide a mobile device which can be taken along by the patient e.g. for travelling in case a constant treatment plan must be met, a mobile source of energy such as an accumulator is provided which enables the device to be operated under conditions in which no external source of energy is present. The capacity of the accumulator is preferably chosen such that the patient can continue the treatment according to the regular treatment plan or prescription.

For a mobile device the positive airway pressure device 2 as such as well as the source of nitric oxide is preferably provided for with a small form factor. To provide a small form factor, it is preferred that the source of nitric oxide is a cylinder with 100-10.000 ppm nitric oxide, preferably 1.000-10.000 ppm. The nitric oxide is preferably provided in a carrier gas such as nitrogen.

LIST OF REFERENCE NUMERALS 1 device for the treatment of respiratory disorders
2 positive airway pressure device
20 patient interface
22 source of breathing gas
24 pressure relief valve
26 hose
3 source of gaseous nitric oxide
30 output line
32 waste gas treatment
4 gas injector
40 mixing channel
5 flow rate sensor
6 controller
60 data communication module
62 compliance module
7 gas sensor
70 sample gas conduit
8 oxygen injector
80 oxygen supply
90 purging input line
92 purging output line
I inhalation phase
II exhalation phase
III inhalation phase
T threshold
P Pulse

The invention claimed is:

1. A method for the treatment of respiratory disorders, the treatment of complications arising from respiratory disorders, or the treatment of secondary respiratory disorders caused by bacterial, viral, protozoal, fungal and/or microbial infections in a mammal; said method comprising:
 providing a device for the treatment of respiratory disorders, the treatment of complications arising from respiratory disorders, or the treatment of secondary respiratory disorders, said device comprising:
  a positive airway pressure device for providing a breathing gas under a positive pressure to a patient interface;
  a source of nitric oxide for providing gaseous nitric oxide;
  a gas injector for injecting nitric oxide provided by the source of nitric oxide into the breathing gas provided by the positive airway pressure device under pressure;
  a flow rate sensor for sensing the flow rate of the breathing gas provided to the patient interface under positive airway pressure; and
  a controller programmed for controlling the gas injector for injecting the nitric oxide into the breathing gas provided by the positive airway pressure device when a flow rate detected by the flow rate sensor exceeds a predetermined threshold flow rate wherein the controller is programmed to control the gas injector to inject the nitric oxide to achieve a concentration of nitric oxide in the breathing gas of between 40 ppm and 1000 ppm, and wherein the controller is programmed to control the positive airway pressure device and the gas injector to inject the nitric oxide into the breathing gas during an interval having a duration of between 1 minute to 60 minutes, with said interval provided at a frequency greater than or equal to every second day and lesser than or equal to 5 intervals a day; and
 producing an inhalable medicament comprising gaseous nitric oxide with the device for the treatment of complications arising from, and/or preventing respiratory disorders; and
 providing the inhalable medicament to an airway of the mammal under positive airway pressure.

2. The method of claim 1, wherein the controller is programmed to control the gas injector to inject the nitric oxide such that a concentration of the nitric oxide is present in the inhalable medicament with a concentration of between 40 ppm and 1000 ppm.

3. The method of claim 1, wherein said respiratory disorders, said complications arising from respiratory disorders, or said secondary respiratory disorders caused by bacterial, viral, protozoal, fungal and/or microbial infections are selected from the group consisting of: a ventilator associated pneumonia (VAP), a toxoplasmosis, a heparin-protamine reaction, a traumatic injury, a traumatic injury to the respiratory tract, acidosis or sepsis, acute mountain sickness, acute pulmonary edema, acute pulmonary hypertension, acute pulmonary thromboembolism, adult respiratory distress syndrome, an acute pulmonary vasoconstriction, aspiration or inhalation injury or poisoning, asthma or status asthmaticus, bronchopulmonary dysplasia, hypoxia or chronic hypoxia, chronic pulmonary hypertension, chronic pulmonary thromboembolism, cystic fibrosis (CF), fat embolism of the lung, haline membrane disease, idiopathic or primary pulmonary hypertension, inflammation of the lung, perinatal aspiration syndrome, persistent pulmonary hypertension of a newborn, post cardiac surgery, a bacterial-, viral- and/or fungal bronchiolitis, a bacterial-, viral- and/or fungal pharyngitis and/or laryngotracheitis, a bacterial-, viral- and/or fungal pneumonia, a bacterial-, viral- and/or fungal sinusitis, a bacterial-, viral- and/or fungal upper and/or lower respiratory tract infection, a bacterial-, viral- and/or fungal-exacerbated asthma, a respiratory syncytial viral infection, bronchiectasis, bronchitis, chronic obstructive lung disease (COPD), cystic fibrosis (CF), emphysema, otitis, otitis media, primary ciliary dyskinesia (PCD), and pulmonary aspergillosis (ABPA) and cryptococcosis.

4. The method of claim 1, further comprising programming the controller to control the gas injector to inject nitric oxide in the concentration of between 80 ppm and 220 ppm into the breathing gas of a positive airway pressure device.

5. The method according to claim 4, characterized in that the nitric oxide is injected in at least one of a single pulse, multiple subsequent pulses of equal or varying width, or as a constant flow with a varying or fixed flow rate.

6. The method according to claim 5, characterized in that the nitric oxide is injected into a flow of breathing gas which is provided under positive airway pressure and the nitric oxide is injected together with a carrier gas.

7. The method according to claim 4, characterized in that the nitric oxide is injected into the breathing gas of the positive airway pressure device only when a predetermined breathing gas flow rate is exceeded or if the pressure in a patient interface falls below a predetermined pressure.

8. The method according to claim 4, characterized in that additional oxygen is injected into the flow of breathing gas.

9. A device for the treatment of respiratory disorders, the treatment of complications arising from respiratory disorders, or the treatment of secondary respiratory disorders, said device comprising:
 a positive airway pressure device for providing a breathing gas under a positive pressure to a patient interface;

a source of nitric oxide for providing gaseous nitric oxide;
a gas injector for injecting nitric oxide provided by the source of nitric oxide into the breathing gas provided by the positive airway pressure device under pressure;
a flow rate sensor for sensing the flow rate of the breathing gas provided to the patient interface under positive airway pressure; and
a controller programmed for controlling the gas injector for injecting the nitric oxide into the breathing gas provided by the positive airway pressure device when a flow rate detected by the flow rate sensor exceeds a predetermined threshold flow rate, wherein the controller is programmed to control the gas injector to inject the nitric oxide to achieve a concentration of nitric oxide in the breathing gas of between 40 ppm and 1000 ppm, and wherein the controller is programmed to control the positive airway pressure device and the gas injector to inject the nitric oxide into the breathing gas during an interval having a duration of between 1 minute to 60 minutes, with said interval provided at a frequency greater than or equal to every second day and lesser than or equal to 5 intervals a day.

10. The device according to claim 9, characterized in that the controller is programmed to control the gas injector to inject the nitric oxide in at least one of a single pulse, in two pulses or in multiple subsequent pulses of equal or varying width, or as a constant flow with a varying or fixed flow rate.

11. The device according to claim 9, characterized in that the controller is programmed to control the gas injector to inject the nitric oxide such that the concentration of nitric oxide in the breathing gas is between 80 ppm and 440 ppm.

12. The device according to claim 9, characterized in that the controller is programmed to determine the onset of inspiration of a patient on the basis of the flow rate sensed by the flow rate sensor and to control the injection of the nitric oxide into the breathing gas on this basis or after a predetermined delay.

13. The device according to claim 9, characterized in that the controller is programmed to control the positive airway pressure device and the gas injector to provide the breathing gas under positive pressure without supplying nitric oxide between the intervals.

14. The device according to claim 9, characterized in that a gas sensor for determining the concentration of nitric oxide, oxygen or nitrogen dioxide in the patient interface is present and the gas sensor is connected to the controller to adjust the concentration of nitric oxide injected accordingly.

15. The device according to claim 9, characterized in that the patient interface comprises a purging means for purging the patient interface with a purging gas.

* * * * *